United States Patent
Remick

(10) Patent No.: US 11,820,754 B2
(45) Date of Patent: Nov. 21, 2023

(54) POLYMORPHS OF AN SSAO INHIBITOR

(71) Applicant: Eli Lilly and Company, Indianapolis, IN (US)

(72) Inventor: David Michael Remick, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/445,792

(22) Filed: Aug. 24, 2021

(65) Prior Publication Data

US 2022/0089563 A1     Mar. 24, 2022

Related U.S. Application Data

(60) Provisional application No. 63/070,147, filed on Aug. 25, 2020.

(51) Int. Cl.
  *C07D 401/04* (2006.01)
  *C07C 309/30* (2006.01)

(52) U.S. Cl.
  CPC .......... *C07D 401/04* (2013.01); *C07C 309/30* (2013.01); *C07B 2200/13* (2013.01)

(58) Field of Classification Search
  CPC .. C07D 401/04; C07C 309/30; C07B 2200/13
  See application file for complete search history.

(56) References Cited

U.S. PATENT DOCUMENTS

| | | | |
|---|---|---|---|
| 8,153,624 B2 | 4/2012 | Genin et al. | |
| 8,426,587 B2 | 4/2013 | McDonald et al. | |
| 8,716,470 B2 | 5/2014 | Yoshihara et al. | |
| 8,785,408 B2 | 7/2014 | Feinstein et al. | |
| 9,302,986 B2 | 4/2016 | Deodhar et al. | |
| 9,714,231 B2 | 7/2017 | Ellsworth et al. | |
| 10,278,970 B2 | 5/2019 | Fan et al. | |
| 10,287,270 B2 * | 5/2019 | Coates | A61P 1/16 |
| 10,464,928 B2 | 11/2019 | Coates et al. | |
| 10,471,060 B2 | 11/2019 | Fan et al. | |
| 10,793,552 B2 | 10/2020 | Coates et al. | |
| 2007/0293548 A1 | 12/2007 | Wang et al. | |
| 2010/0152166 A1 | 6/2010 | Genin et al. | |
| 2012/0016119 A1 | 1/2012 | Tsuboi et al. | |
| 2014/0275063 A1 | 9/2014 | Carley et al. | |
| 2014/0315882 A1 | 10/2014 | Fleck et al. | |
| 2014/0343083 A1 | 11/2014 | Heine et al. | |
| 2016/0024080 A1 | 1/2016 | Patient et al. | |
| 2018/0296560 A1 | 10/2018 | Fan et al. | |
| 2018/0297987 A1 | 10/2018 | Coates et al. | |
| 2019/0111012 A1 | 4/2019 | Hanf | |
| 2019/0247404 A1 | 8/2019 | Namisaki et al. | |
| 2019/0275041 A1 | 9/2019 | Fan et al. | |
| 2019/0276436 A1 | 9/2019 | Coates et al. | |
| 2019/0321364 A1 | 10/2019 | Satyal et al. | |
| 2020/0054589 A1 | 2/2020 | Noel et al. | |
| 2020/0190064 A1 | 6/2020 | Yu et al. | |
| 2020/0262817 A1 | 8/2020 | Coates et al. | |
| 2020/0397798 A1 | 12/2020 | Mohan et al. | |
| 2021/0121493 A1 | 4/2021 | Noureddin et al. | |
| 2021/0379040 A1 | 12/2021 | Fenaux et al. | |
| 2021/0379043 A1 | 12/2021 | Fenaux et al. | |
| 2022/0265614 A1 | 8/2022 | Brees et al. | |
| 2023/0127498 A1 | 4/2023 | Fenaux et al. | |

FOREIGN PATENT DOCUMENTS

| | | |
|---|---|---|
| CN | 103459369 A | 12/2013 |
| CN | 104520268 A | 4/2015 |
| CN | 105121426 A | 12/2015 |
| CN | 108341752 A | 7/2018 |
| CN | 109251166 A | 1/2019 |
| EP | 3437659 A1 | 2/2019 |
| JP | 2010533658 A | 10/2010 |
| JP | 2011034078 A | 2/2011 |
| JP | 2011504485 A | 2/2011 |
| JP | 2011136942 A | 7/2011 |
| JP | 2015521167 A | 7/2015 |
| JP | 2019527717 A | 10/2019 |
| WO | WO-2007120528 A2 | 10/2007 |
| WO | WO-2008123469 A1 | 10/2008 |
| WO | WO-2009012573 A1 | 1/2009 |
| WO | WO-2009066152 A2 | 5/2009 |
| WO | WO-2012124696 A1 | 9/2012 |
| WO | WO-2013163675 A1 | 11/2013 |
| WO | WO-2014078609 A1 | 5/2014 |
| WO | WO-2015058160 A1 | 4/2015 |
| WO | WO-2016042332 A1 | 3/2016 |
| WO | WO-2017167935 A1 | 10/2017 |
| WO | WO-2018027892 A1 | 2/2018 |

(Continued)

OTHER PUBLICATIONS

Alberts, W. M., "The Outlook for Survivors of ARDS," American College of Chest Physicians, vol. 84(3), p. 272-274 (Sep. 1983).
Ashburner M., et al., "Gene Ontology: Tool for the Unification of Biology. The Gene Ontology Consortium," Nature Genetics, May 2000, vol. 25, pp. 25-29.
Brecher, J., "Graphical Representation of Stereochemical Configuration (IUPAC Recommendations 2006)," Pure and Appl. Chem. 78(10):1897-1970 (2006).
Chen, H.C. et al. (Nov. 13-16, 2020). MET409, an Optimized Sustained FXR Agonist, Was Safe and Well-Tolerated in a 14-Day Phase 1 Study in Healthy Subjects, Me0.tacrine, 1 page, Poster presented at Poster presentation at EASL—The International Liver Congress, Apr. 2019, Vienna, Austria.
Chung D., et al., "Pharmacokinetics of Two Oral Formulations of Liver-directed, Nonsteroidal Farnesoid X- Receptor Agonist Tern-101 in Healhy Volunteers," Terns Pharmaceutical, Inc., Poster presented at Paris NASH Meeting, Oct. 22-23, 2020, 1 Page.

(Continued)

*Primary Examiner* — Susanna Moore
*Assistant Examiner* — Luisalberto Gonzalez
(74) *Attorney, Agent, or Firm* — COOLEY LLP; Heidi A. Erlacher; Eric A. Owens

(57) ABSTRACT

Provided herein are polymorphs of (2E)-3-fluoro-2-({[2-(4-methoxypiperidin-1-yl)pyrimidin-5-yl]oxy}methyl)prop-2-en-1-aminium 4-methylbenzenesulfonate, compositions thereof, methods of preparation thereof, and methods of use thereof.

18 Claims, 3 Drawing Sheets

(56) References Cited

FOREIGN PATENT DOCUMENTS

| WO | WO-2018028517 A1 | 2/2018 |
|---|---|---|
| WO | WO-2018073154 A1 | 4/2018 |
| WO | WO-2018103624 A1 | 6/2018 |
| WO | WO-2018148856 A1 | 8/2018 |
| WO | WO-2018149226 A1 | 8/2018 |
| WO | WO-2018151985 A1 | 8/2018 |
| WO | WO-2018153933 A1 | 8/2018 |
| WO | WO-2018167103 A1 | 9/2018 |
| WO | WO-2018170173 A1 | 9/2018 |
| WO | WO-2018193006 A1 | 10/2018 |
| WO | WO-2018193007 A1 | 10/2018 |
| WO | WO-2019023245 A1 | 1/2019 |
| WO | WO-2019038456 A1 | 2/2019 |
| WO | WO-2019053233 A1 | 3/2019 |
| WO | WO-2019053235 A1 | 3/2019 |
| WO | WO-2019094777 A1 | 5/2019 |
| WO | WO-2019241751 A1 | 12/2019 |
| WO | WO-2020042114 A1 | 3/2020 |
| WO | WO-2020061114 A1 | 3/2020 |
| WO | WO-2020063696 A1 | 4/2020 |
| WO | WO-2020086747 A2 | 4/2020 |
| WO | WO-2020089025 A1 | 5/2020 |
| WO | WO-2020131578 A2 | 6/2020 |
| WO | WO-2021014350 A1 | 1/2021 |
| WO | WO-2021195435 A1 | 9/2021 |
| WO | WO-2021231644 A1 | 11/2021 |
| WO | WO-2021231646 A1 | 11/2021 |
| WO | WO-2022046779 A1 | 3/2022 |
| WO | WO-2023086561 A1 | 5/2023 |
| WO | WO-2023086562 A1 | 5/2023 |

OTHER PUBLICATIONS

Dufour J-F., et al., "Combination Therapy for Non-Alcoholic Steatohepatitis: Rationale, Opportunities and Challenges," Gut, Oct. 2020, vol. 69, No. 10, pp. 1877-1884.

Dunkel, P. et al., "Semicarbazide-sensitive amine oxidase/vascular adhesion protein-1: a patent survey," Expert Opinion on Therapeutic Patents, vol. 21, No. 9, pp. 1453-1471, doi:10.1517/13543776.2011. 594040 (Jun. 2011).

Extended European Search Report for European Application No. 17838647.0, dated Feb. 20, 2020, 7 Pages.

Extended European Search Report for European Application No. 21206067.7, dated Feb. 18, 2022, 7 Pages.

Foot, J. J. et al., "PXS-4681A, a Potent and Selective Mechanism-Based Inhibitor of SSAO/VAP-1 with Anti-Inflammatory Effects In Vivo," J Pharmacol Exp Ther, 347, pp. 365-374, Nov. 2013, http://dx.doi.org/10.1124/jpet.113.207613.

Franks, T. J. et al., "Lung Pathology of Severe Acute Respiratory Syndrome (SARS): A Study of 8 Autopsy Cases from Singapore," Human Pathology, vol. 34, No. 8, pp. 743-748, Aug. 2003, doi: 10.1016/S0046-8177(03)00367-8, including Update, vol. 35(1), p. 139, Jan. 2004, https://doi.org/10.1016/S0046-8177(04)00002-4.

Genenome Ontology Consortium., "Creating the Gene Ontology Resource: Design and Implementation," Genome Research, Aug. 2001, vol. 11, No. 8, pp. 1425-1433.

Gonzalez, JN, et al., "The Acute Respiratory Distress Syndrome: Mechanisms and Perspective Therapeutic Approaches," Austin Journal of Vascular Medicine 2015, vol. 2, Issue 1, 1009, 6 pages.

Han C.Y., "Update on FXR Biology: Promising Therapeutic Target?," International Journal of Molecular Sciences, Jul. 16, 2018, vol. 19, No. 2069, 25 pages.

International Preliminary Report on Patentability for International Application No. PCT/CN2016/094833, dated Feb. 21, 2019, 7 Pages.

International Preliminary Report on Patentability for International Application No. PCT/CN2017/000157, dated Aug. 29, 2019, 6 Pages.

International Preliminary Report on Patentability for International Application No. PCT/CN2017/095999, dated Feb. 21, 2019, 6 Pages.

International Preliminary Report on Patentability for International Application No. PCT/CN2017/117791, dated Aug. 29, 2019, 6 Pages.

International Preliminary Report on Patentability for International Application No. PCT/CN2018/103349, dated Mar. 11, 2021, 7 Pages.

International Preliminary Report on Patentability for International Application No. PCT/US2008/069719, dated Jan. 19, 2010, 7 Pages.

International Preliminary Report on Patentability for International Application No. PCT/US2018/017152, dated Aug. 29, 2019, 7 Pages.

International Search Report and Written Opinion for International Application No. PCT/CN2016/094833, dated May 16, 2017, 10 Pages.

International Search Report and Written Opinion for International Application No. PCT/CN2017/000157, dated Nov. 22, 2017, 8 Pages.

International Search Report and Written Opinion for International Application No. PCT/CN2017/095999, dated Nov. 13, 2017, 8 Pages.

International Search Report and Written Opinion for International Application No. PCT/CN2017/117791, dated Mar. 29, 2018, 8 Pages.

International Search Report and Written Opinion for International Application No. PCT/CN2018/103349, dated Jun. 5, 2019, 9 Pages.

International Search Report and Written Opinion for International Application No. PCT/US2008/069719, dated Nov. 6, 2008, 9 Pages.

International Search Report and Written Opinion for International Application No. PCT/US2018/017152, dated Apr. 20, 2018, 9 Pages.

International Search Report and Written Opinion for International Application No. PCT/US2020/059522, dated Feb. 5, 2021, 9 Pages.

International Search Report and Written Opinion for International Application No. PCT/US2021/032083, dated Sep. 29, 2021, 16 Pages.

International Search Report and Written Opinion for International Application No. PCT/US2021/047363, dated Dec. 16, 2021, 9 Pages.

International Search Report and Written Opinion, dated Jun. 8, 2021, for International Application No. PCT/US2021/024239 (7 total pages).

Invitation to Pay Additional Fees, and, Where Applicable, Protest Fee, dated Jul. 6, 2021, for International Application No. PCT/US2021/032083 (3 total pages).

Invitation to Pay Additional Fees, dated Jul. 6, 2021, for PCT Application No. PCT/US2021/032085, filed May 12, 2021, 3 pages.

Jarnicki, A. G., et al., "The inhibitor of semicarbazide-sensitive amine oxidase, PXS-4728A, ameliorates key features of chronic obstructive pulmonary disease in a mouse model," British Journal of Pharmacology (2016), 173, 3161-3175, DOI:10.1111/bph.13573.

Jarolimek, W. et al., "Phase 1 results from PXS-4728A, a selective SSAO/VAP-1 inhibitor, for the treatment of non-alcoholic steatohepatitis," Journal of Hepatology, Dec. 2015, vol. 62, pp. s274-s275 (Abstract LP22).

Kawamata, Y., et al. "AG protein-coupled receptor responsive to bile acids", The Journal of Biological Chemistry, 278(11):9435-9440 (Mar. 2003).

Kelly, M. J., et al., "Discovery of 2-[3,5-Dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor β Agonist in Clinical Trials for the Treatment of Dyslipidemia," Journal of Medicinal Chemistry, 2014, 57, 10, 3912-3923, https://doi.org/10.1021/jm4019299.

Kinoshita, T. et al., Inhibition of Vascular Adhesion Protein-1 Enhances the Anti-Tumor Effects of Immune Checkpoint Inhibitors, Cancer Science, 112, 1390-1401 (2021).

Kremoser C., "FXR Agonists for NASH: How Are They Different and What Difference Do They Make?," Journal of Hepatology 2021, vol. 75, pp. 12-15.

Lee, Kyung-Yil, "Pneumonia, Acute Respiratory Distress Syndrome, and Early Immune-Modulator Therapy," Int. J. Mol. Sci. 2017, 18, 388, 15 pages, doi: 10.3390/ijms18020388.

(56) References Cited

OTHER PUBLICATIONS

Liao M., et al., "The landscape of lung bronchoalveolar immune cells in COVID-19 revealed by single-cell RNA sequencing," Feb. 2020, 23 pages, https://doi.org/10.1101/2020.02.23.20026690.

Obach R.S., et al., "The Prediction of Human Pharmacokinetic Parameters From Preclinical and In Vitro Metabolism Data," Journal of Pharmacology and Experimental Therapeutics, Oct. 1997, vol. 283, No. 1, pp. 46-58.

Reagan-Shaw, S., et al., "Dose translation from animal to human studies revisited," The FASEB Journal, vol. 22, pp. 659-661 (Mar. 2007).

Salter-Cid, L. M. et al., "Anti-Inflammatory Effects of Inhibiting the Amine Oxidase Activity of Semicarbazide-Senstive Amine Oxidase," The Journal of Pharmacology and Experimental Therapeutics 2005, vol. 315, No. 2, pp. 553-562, doi:10.1124/jpet.105.089649.

Schilter, H. C., et al., "Effects of an anti-inflammatory VAP-1/SSAO inhbitor, PXS-4728A, on pulmonary neutrophil migration, Respiratory Research (2015), 16:42, 14 pages, DOI 10.1186/s12931-015-0200-z.

Schwimmer J.B., et al., "Prevalence of Fatty Liver in Children and Adolescents," Pediatrics, Oct. 2006, vol. 118, No. 4, pp. 1388-1393.

Shepherd E.L., et al., "Inhibition of Vascular Adhesion Protein-1 Modifies Hepatic Steatosis In Vitro and In Vivo," World Journal of Hepatology, Nov. 27, 2020, vol. 12, No. 11, pp. 931-948.

Tian, S et al., "Pulmonary Pathology of Early-Phase 2019 Novel Coronavirus (COVID-19) Pneumonia in Two Patients With Lung Cancer," Journal of Thoracic Oncology, May 2020, vol. 15, No. 5, pp. 700-704, http://doi.org/10.1016/j.jtho.2020.02.010.

Tsui, P. T., et al., "Severe Acute Respiratory Syndrome: Clinical Outcome and Prognostic Correlates," Emerging Infectious Diseases, vol. 9, No. 9, Sep. 2003, pp. 1064-1069.

Walsh, K., et al., Amination of Heteroaryl Chlorides: Palladium Catalysis or SNAr in Green Solvents? ChemSusChem, 6(8), pp. 1455-1460, doi: 10.1002/cssc.201300239 (2013).

Wang, Y. et al. "Enantioselective CuH-Catalyzed Hydroallylation of Vinylarenes," Journal of the American Chemical Society, vol. 138, No. 15, pp. 5024-5027 (Apr. 2016).

Weston, C. J., et al., Hepatic consequences of vascular adhesion protein-1 expression, J. Nerual. Transm. (2011), 118:1055-1064, DOI: 10.1007/s00702-011-0647-0.

Weston C.J., et al., "Vascular Adhesion Protein-1 Promotes Liver Inflammation and Drives Hepatic Fibrosis," The Journal of Clinical Investigation, Feb. 2015, vol. 125, No. 2, pp. 501-520.

Yoshida, K., et al., "Reaction of N-substituted cyclic amines with 2,4-dichloropyrimidine, and its 5-methyl derivative," Journal of Chemical Society, Perkin Transactions 1, pp. 919-922 (1992).

Fiorucci, S., et al., "Future trends in the treatment of nonalcoholic steatohepatitis," Pharmacological Research, Jul. 2018, vol. 134, pp. 289-298, doi: 10.1016/J. PHRS.2018.07.014.

International Preliminary Report on Patentability, dated Oct. 6, 2022, for International Application No. PCT/US2021/024239 (6 total pages).

International Search Report and Written Opinion for International Application No. PCT/US2022/049690 dated Mar. 16, 2023, 21 pages.

International Search Report and Written Opinion for International Application No. PCT/US2022/049692 dated Mar. 17, 2023, 18 pages.

Noureddin, M., et al., "Favorable Safety Profile Of Tern-201, A Highly Selective Inhibitor Of Vascular Adhesion Protein-1, In The Nonalcoholic Steatohepatitis Phase 1b Aviation Study Poster No. Sat-142 Figure 2: Study Design Acknowledgements," EASL International Liver Congress, Jun. 26, 2022, 1 page, DOI: 10.3252/pso.eu.ILC2022.2022.

Vuppalanchi, R., et al., "Therapeutic pipeline in nonalcoholic steatohepatitis," Nature Reviews Gastroenterology, Feb. 2021, vol. 18, No. 6, pp. 373-392, doi: 10.1038/S41575-020-00408-Y.

\* cited by examiner

POLYMORPHS OF AN SSAO INHIBITOR

CROSS-REFERENCE TO RELATED APPLICATIONS

This application claims priority to U.S. Provisional Patent Application No. 63/070,147, filed Aug. 25, 2020, the disclosure of which is hereby incorporated by reference in its entirety for all purposes.

FIELD

Provided herein are polymorphs of (2E)-3-fluoro-2-({[2-(4-methoxypiperidin-1-yl)pyrimidin-5-yl]oxy}methyl)prop-2-en-1-aminium 4-methylbenzenesulfonate, compositions thereof, methods of preparation thereof, and methods of use thereof.

BACKGROUND

Semicarbazide-sensitive amino oxidase/vascular adhesion protein-1 (SSAO/VAP-1) is a member of the semicarbazide-sensitive amino oxidase family. SSAO/VAP-1 has been alternatively referred to as VAP-1 or SSAO. SSAO/VAP-1 is an enzyme that exists both as a membrane-bound and a soluble isoform; it is predominantly expressed from endothelial cell surface, vascular smooth muscle and adipose cells. SSAO/VAP-1 participates in many cellular processes including glucose disposition, inflammation responses, and leukocyte recruitment. High activity levels of this enzyme are associated with diabetes, atherosclerosis, strokes, chronic kidney disease, and Alzheimer's disease, among other disorders. Recently SSAO/VAP-1 has been implicated in the pathogenesis of liver disorders such as fatty liver disease. U.S. Pat. No. 10,287,270, the content of which is incorporated herein by reference in its entirety, discloses (2E)-3-fluoro-2-({[2-(4-methoxypiperidin-1-yl)pyrimidin-5-yl]oxy}methyl)prop-2-en-1-amine (designated herein as "Compound I") and a polymorphic form of (2E)-3-fluoro-2-({[2-(4-methoxypiperidin-1-yl)pyrimidin-5-yl]oxy}methyl)prop-2-en-1-aminium 4-methylbenzenesulfonate ((2E)-3-fluoro-2-({[2-(4-methoxypiperidin-1-yl)pyrimidin-5-yl]oxy}methyl)prop-2-en-1-aminium 4-methylbenzenesulfonate is designated herein as "Compound I tosylate" and the polymorphic form is designated herein as "Form I"), the structures of which are provided below.

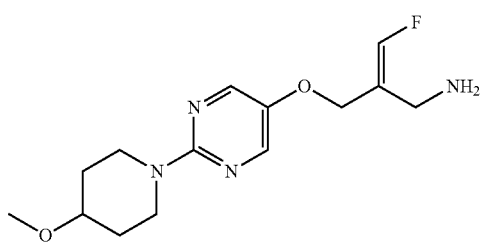

Compound I

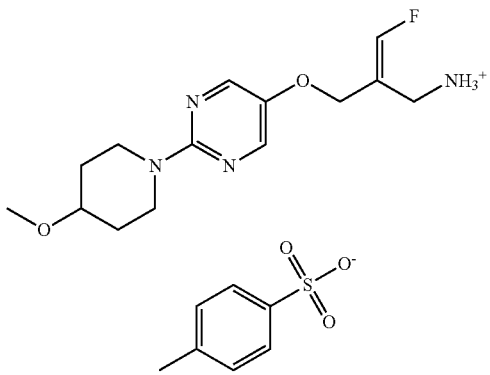

Compound I tosylate

Compound I is a potent SSAO inhibitor being developed as a therapeutic for liver disorders. To move a drug candidate such as Compound I to a viable pharmaceutical product, it can be important to understand whether the drug candidate or its salt form has polymorphic forms, as well as the relative stability and interconversions of these forms under conditions likely to be encountered upon large-scale production, transportation, storage, and pre-usage preparation. The ability to control and produce a stable polymorph with a robust manufacturing process can be key for regulatory approval and marketing. Large-scale production processes for high purity Compound I can be improved by use of particular polymorphic forms. Accordingly, there is a need for various new polymorphic forms of Compound I or its salt form with different chemical and physical stabilities, and compositions and uses of the same.

BRIEF SUMMARY

In one aspect, provided herein is a polymorph of Compound I tosylate.

In another aspect, provided herein are methods of preparing a polymorph of Compound I tosylate.

In another aspect, provided herein are compositions comprising a polymorph of Compound I tosylate.

In another aspect, provided herein are methods of treating a subject in need of treatment of liver disorders using a polymorph of Compound I tosylate. Also provided is use of a polymorph of Compound I tosylate in the manufacture of a medicament for treating liver disorders.

DETAILED DESCRIPTION

Definitions

Figure 1:
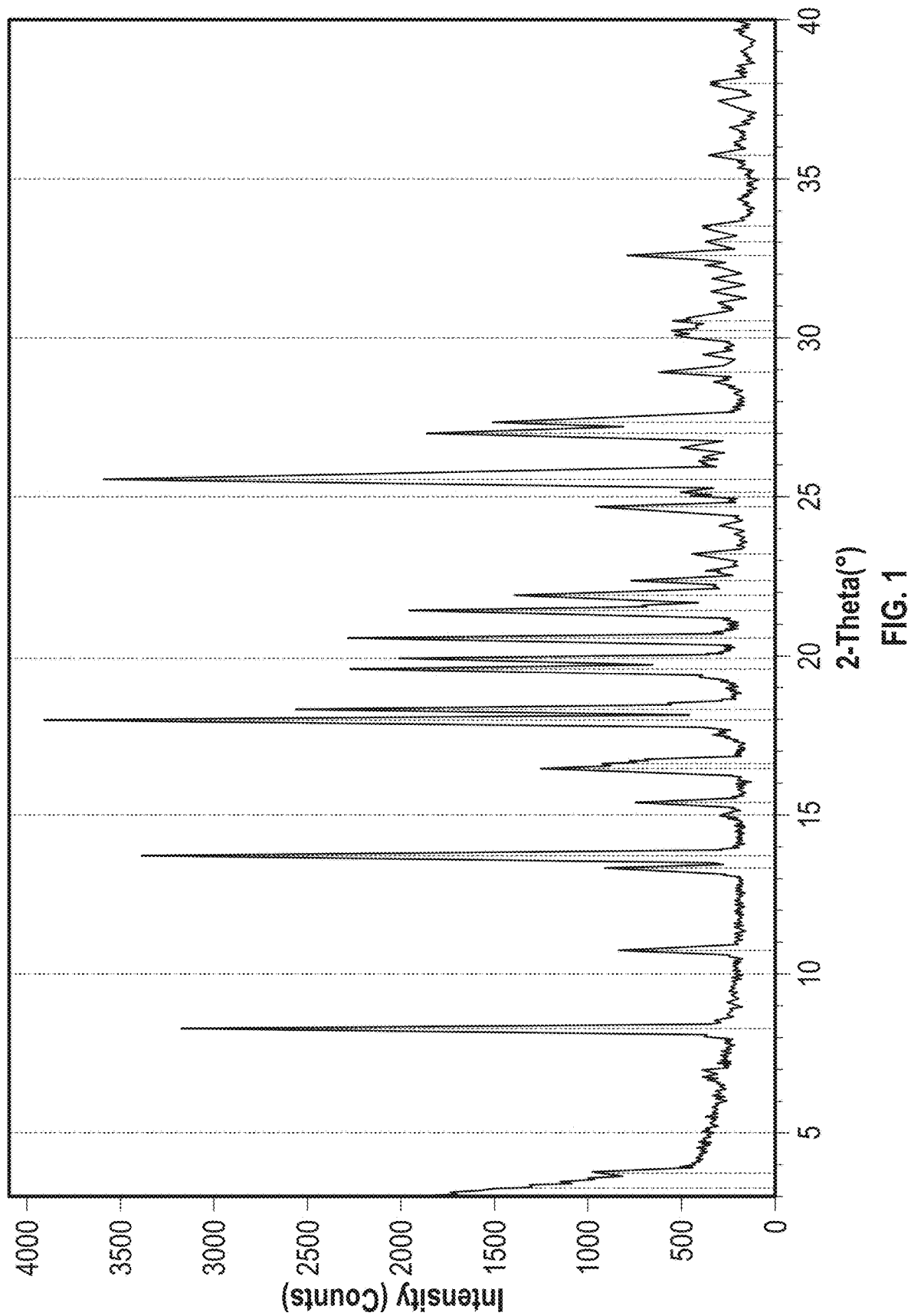
FIG. 1 shows an X-ray powder diffraction (XRPD) pattern of polymorphic Form II of Compound I tosylate (Form II).

As used herein and in the appended claims, the singular forms "a", "an" and "the" include plural forms, unless the context clearly dictates otherwise.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in connection with a value, contemplate a variation within ±15%, within ±10%, within ±5%, within ±4%, within ±3%, within ±2%, within ±1%, or within ±0.5% of the specified value. Reference to "about" a value or parameter herein includes (and describes) embodiments that are directed to that value or parameter per se. For example, description referring to "about X" includes description of "X".

As used herein, the term "polymorph" or "polymorphic form" refers to a crystalline form of a compound. Different polymorphs may have different physical properties such as, for example, melting temperatures, heats of fusion, solubilities, dissolution rates, and/or vibrational spectra as a result of the arrangement or conformation of the molecules or ions in the crystal lattice. The differences in physical properties exhibited by polymorphs may affect pharmaceutical parameters, such as storage stability, compressibility, density (important in formulation and product manufacturing), and dissolution rate (an important factor in bioavailability).

As used herein, the term "pharmaceutically acceptable carrier," and cognates thereof, refers to adjuvants, binders, diluents, etc. known to the skilled artisan that are suitable for administration to an individual (e.g., a mammal or non-mammal). Combinations of two or more carriers are also contemplated. The pharmaceutically acceptable carrier(s) and any additional components, as described herein, should be compatible for use in the intended route of administration (e.g., oral or parenteral) for a particular dosage form, as would be recognized by the skilled artisan.

As used herein, "treatment" or "treating" is an approach for obtaining beneficial or desired results including clinical results. For purposes of this disclosure, beneficial or desired results include, but are not limited to, one or more of the following: decreasing one or more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delaying or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of this disclosure contemplate any one or more of these aspects of treatment.

The term "subject" refers to an animal, including, but are not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

As used herein, the term "therapeutically effective amount" refers to an amount of a compound or composition sufficient to treat a specified disorder, condition or disease such as to ameliorate, to palliate, to lessen, and/or to delay one or more of its symptoms.

As used herein, the term "substantially as shown in" when referring, for example, to an XRPD pattern, a DSC graph, or a TGA graph, includes a pattern or graph that is not necessarily identical to those depicted herein, but falls within the limits of experimental errors or deviations when considered by one of ordinary skill in the art.

As used herein, the term "substantially free of" means that the composition contains the indicated substance or substances in an amount of less than about 25%, less than about 20%, less than about 15%, less than about 10%, less than about 5%, less than about 4%, less than about 3%, less than about 2%, or less than about 1% by weight.

Polymorphs

In one aspect, provided herein is a polymorph of Compound I tosylate, which has the structure shown below.

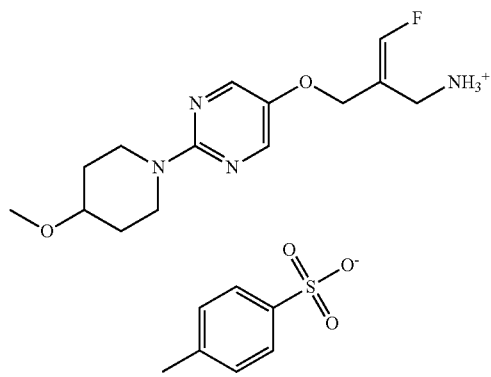

Compound I tosylate

A polymorph of Compound I or a salt thereof may provide the advantages of bioavailability and stability and may be suitable for use as an active agent in a pharmaceutical composition. Variations in the crystal structure of a pharmaceutical drug substance may affect the dissolution rate (which may affect bioavailability, etc.), manufacturability (e.g., ease of handling, ease of purification, ability to consistently prepare doses of known strength, etc.) and stability (e.g., thermal stability, shelf life (including resistance to degradation), etc.) of a pharmaceutical drug product. Such variations may affect the methods of preparation or formulation of pharmaceutical compositions in different dosage or delivery forms, such as solid oral dosage forms including tablets and capsules. Compared to other forms such as non-crystalline or amorphous forms, polymorphs may provide desired or suitable hygroscopicity, particle size control, dissolution rate, solubility, purity, physical and chemical stability, manufacturability, yield, reproducibility, and/or process control. Thus, polymorphs of Compound I may provide advantages of improving the manufacturing process of an active agent or the stability or storability of a drug product form of the active agent, or having suitable bioavailability and/or stability as an active agent.

The use of certain conditions, such as the use of different solvents and/or temperatures, has been found to produce different polymorphs of Compound I or a salt thereof, including polymorphic Form II described herein, which may exhibit one or more favorable characteristics described herein.

Form II

In some embodiments, provided herein is polymorphic Form II of Compound I tosylate.

In some embodiments, Form II has an XRPD pattern substantially as shown in FIG. 1. Angles 2-theta and relative peak intensities that may be observed for Form II using XRPD are shown in Table 1.

TABLE 1

| Angle/2θ | Intensity/counts | Intensity % |
|---|---|---|
| 3.2 | 1161 | 31.3 |
| 3.7 | 641 | 17.3 |
| 8.3 | 2944 | 79.4 |
| 10.8 | 635 | 17.1 |
| 13.3 | 729 | 19.7 |
| 13.7 | 3216 | 86.8 |
| 15.4 | 554 | 14.9 |
| 16.5 | 1065 | 28.7 |
| 16.6 | 623 | 16.8 |
| 18.0 | 3707 | 100 |
| 18.3 | 2375 | 64.1 |
| 19.6 | 2048 | 55.2 |
| 19.9 | 1792 | 48.3 |
| 20.6 | 2058 | 55.5 |
| 21.4 | 1735 | 46.8 |
| 21.9 | 1170 | 31.6 |
| 22.4 | 575 | 15.5 |
| 23.2 | 236 | 6.4 |
| 24.7 | 702 | 18.9 |
| 25.1 | 327 | 8.8 |
| 25.5 | 3281 | 88.5 |
| 27.0 | 1680 | 45.3 |
| 27.3 | 1331 | 35.9 |
| 28.9 | 397 | 10.7 |
| 30.2 | 323 | 8.7 |
| 30.5 | 312 | 8.4 |
| 32.6 | 605 | 16.3 |
| 33.5 | 212 | 5.7 |
| 35.7 | 221 | 6 |
| 38.0 | 203 | 5.5 |

In some embodiments, Form II has an XRPD pattern displaying at least two, at least three, at least four, at least five, at least six, at least seven, at least eight, at least nine, at least ten, at least fifteen, or at least twenty of the peaks at angles 2-theta with the greatest intensity in the XRPD pattern as shown in FIG. 1 or as provided in Table 1. It should be understood that relative intensities can vary depending on a number of factors, including sample preparation, mounting, and the instrument and analytical procedure and settings used to obtain the spectrum. Relative peak intensities and peak assignments can vary within experimental error. In some embodiments, peak assignments listed herein can vary by ±0.6 degrees, ±0.4 degrees, ±0.2 degrees, or ±0.1 degrees 2-theta. In some embodiments, peak assignments listed herein, including for Form II, can vary by ±0.6 degrees 2-theta. In some embodiments, peak assignments listed herein can vary by ±0.4 degrees 2-theta. In some embodiments, peak assignments listed herein can vary by ±0.2 degrees 2-theta. In some embodiments, peak assignments listed herein can vary by ±0.1 degrees 2-theta.

In some embodiments, Form II has an XRPD pattern comprising peaks at angles 2-theta of 13.7±0.2, 18.0±0.2, and 25.5±0.2 degrees. In some embodiments, Form II has an XRPD pattern comprising peaks at angles 2-theta of 8.3±0.2, 13.7±0.2, 18.0±0.2, 18.3±0.2, and 25.5±0.2 degrees. In some embodiments, Form II has an XRPD pattern comprising peaks at angles 2-theta of 8.3±0.2, 13.7±0.2, 18.0±0.2, 18.3±0.2, 19.6±0.2, 20.6±0.2, and 25.5±0.2 degrees. In some embodiments, Form II has an XRPD pattern comprising peaks at angles 2-theta of 8.3±0.2, 13.7±0.2, 18.0±0.2, 18.3±0.2, 19.6±0.2, 19.9±0.2, 20.6±0.2, 21.4±0.2, 25.5±0.2, and 27.0±0.2 degrees.

Figure 2:
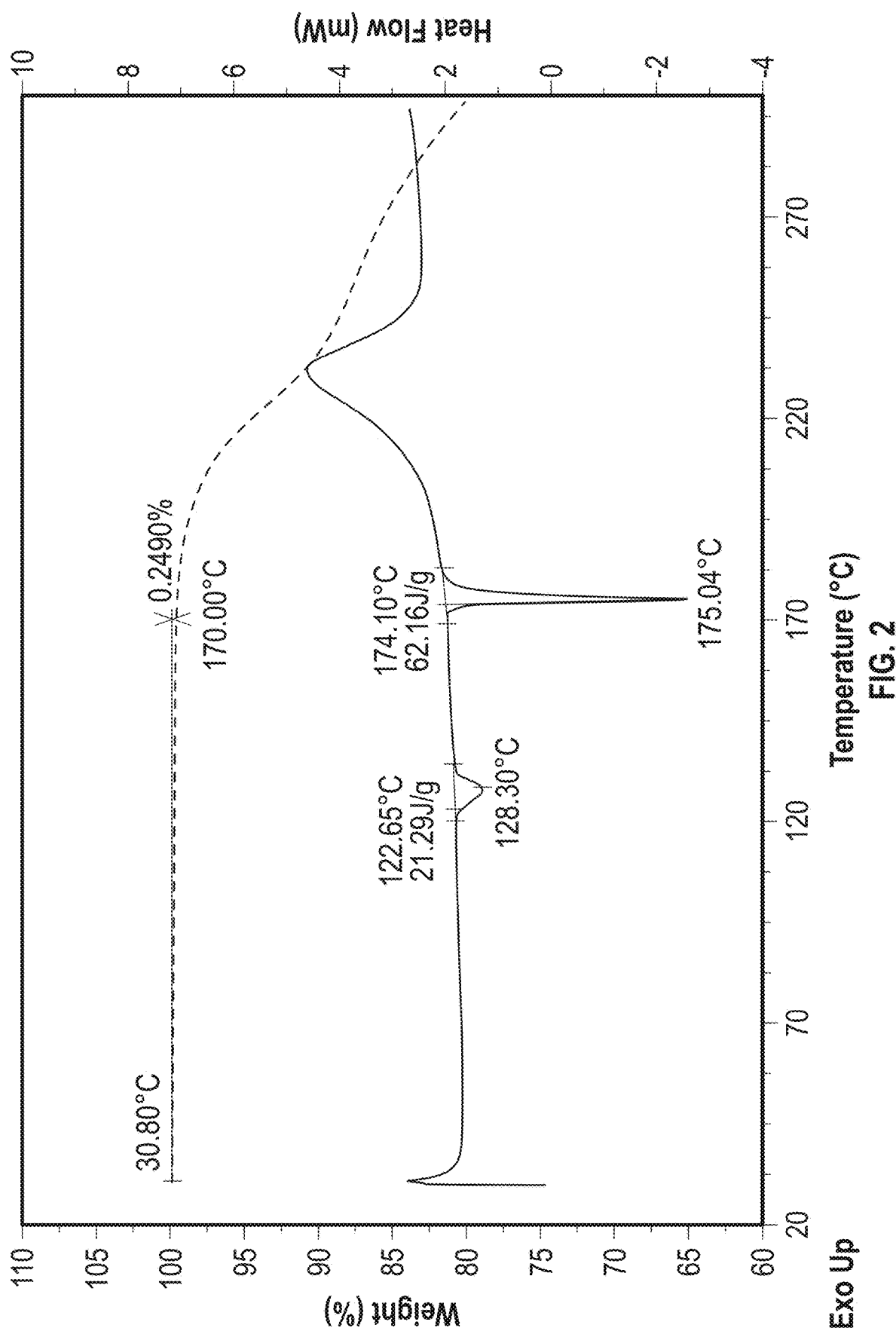
FIG. 2 shows a differential scanning calorimetry (DSC) graph and a thermogravimetric analysis (TGA) graph of Form II.
Figure 3:
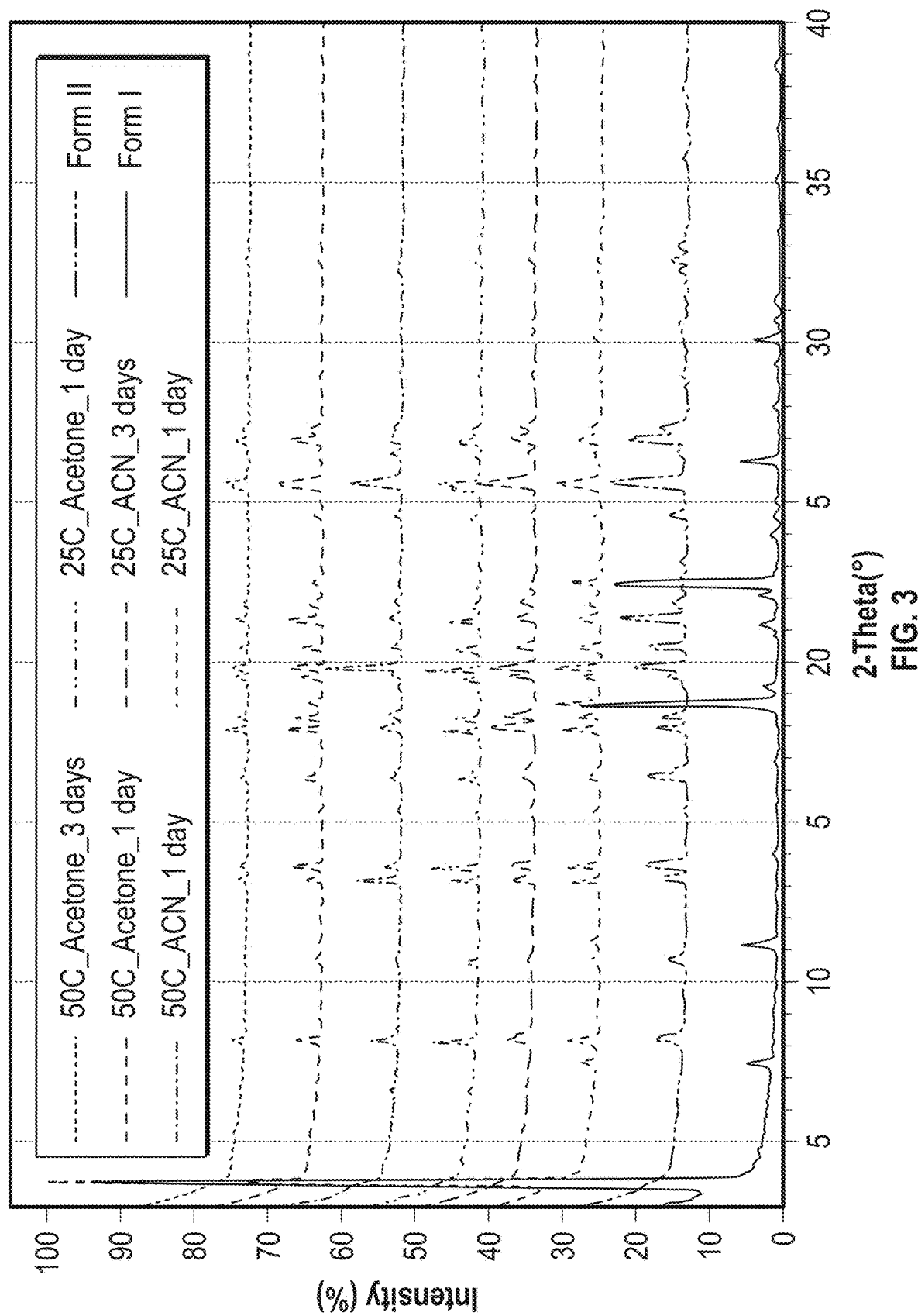
FIG. 3 shows the results of competitive slurry experiments performed at 25° C. and 50° C.

In some embodiments, Form II has a DSC graph substantially as shown in FIG. 2. In some embodiments, Form II is characterized as having an endotherm onset at about 123° C. and/or an endotherm onset at about 174° C. as determined by DSC. In some embodiments, Form II is characterized as having an endotherm onset at 123±5° C., 123±4° C., 123±3° C., 123±2° C., or 123±1° C. as determined by DSC. In some embodiments, Form II is characterized as having an endotherm onset at 174±5° C., 174±4° C., 174±3° C., 174±2° C., or 174±1° C.

In some embodiments, Form II has a TGA graph substantially as shown in FIG. 2.

In some embodiments of Form II, at least one, at least two, at least three, at least four, or all of the following (a)-(e) apply:

(a) Form II has an XRPD pattern comprising peaks at angles 2-theta of 13.7±0.2, 18.0±0.2, and 25.5±0.2 degrees; an XRPD pattern comprising peaks at angles 2-theta of 8.3±0.2, 13.7±0.2, 18.0±0.2, 18.3±0.2, and 25.5±0.2 degrees; an XRPD pattern comprising peaks at angles 2-theta of 8.3±0.2, 13.7±0.2, 18.0±0.2, 18.3±0.2, 19.6±0.2, 20.6±0.2, and 25.5±0.2 degrees; or an XRPD pattern comprising peaks at angles 2-theta of 8.3±0.2, 13.7±0.2, 18.0±0.2, 18.3±0.2, 19.6±0.2, 19.9±0.2, 20.6±0.2, 21.4±0.2, 25.5±0.2, and 27.0±0.2 degrees;

(b) Form II has an XRPD pattern substantially as shown in FIG. 1;

(c) Form II is characterized as having an endotherm onset at about 123° C. and/or an endotherm onset at about 174° C. as determined by DSC;

(d) Form II has a DSC graph substantially as shown in FIG. 2; and (e) Form II has a TGA graph substantially as shown in FIG. 2.

Compositions

In another aspect, provided herein is a composition comprising a polymorphic form disclosed herein. In some embodiments, the composition comprises Form II. In some embodiments, the composition is a pharmaceutical composition. In some embodiments, the composition further comprises a pharmaceutically acceptable carrier. In some embodiments, the composition comprising Form II is substantially free of Form I. In some embodiments, the composition is substantially free of amorphous or non-crystalline form of Compound I.

In some embodiments of the composition comprising Form II, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least 99.9% by weight of the total composition is Form II. In some embodiments of the composition comprising Form II, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least 99.9% by weight of Compound I exists in Form II.

In some embodiments, provided is a tablet or capsule comprising substantially pure Form II, and a pharmaceutically acceptable carrier.

Methods of Preparation

Form II

In some embodiments, provided is a method of preparing Form II, comprising evaporating a solution of Compound I tosylate in a solvent, wherein the solvent comprises acetonitrile (ACN) and water. In some embodiments, the volume ratio of ACN to water is between about 95:5 and about 5:95. In some embodiments, the volume ratio of ACN to water is about 95:5, about 90:10, about 80:20, about 70:30, about 60:40, about 50:50, about 40:60, about 30:70, about 20:80, about 10:90, or about 5:95. In some embodiments, the volume ratio of ACN to water is about 95:5.

In some embodiments, provided is a method of preparing Form II, comprising stirring a mixture comprising Compound I tosylate and a solvent, wherein the solvent comprises ACN and water or the solvent comprises ethyl acetate. In some embodiments, the solvent comprises ethyl acetate. In some embodiments, the solvent comprises ACN and water. In some embodiments, the volume ratio of ACN to water is between about 95:5 and about 5:95. In some embodiments, the volume ratio of ACN to water is about 95:5, about 90:10, about 80:20, about 70:30, about 60:40, about 50:50, about 40:60, about 30:70, about 20:80, about 10:90, or about 5:95. In some embodiments, the volume ratio of ACN to water is about 95:5.

In some embodiments, provided is a method of preparing Form II, comprising adding an anti-solvent to a solution of Compound I tosylate in a solvent, wherein the solvent comprises ACN and water and wherein the anti-solvent comprises 2-methyltetrahydrofuran (2-MeTHF).

Methods of Use

In another aspect, provided herein is a method of treating a liver disorder in a patient (e.g., a human patient) in need thereof comprising administering a therapeutically effective amount of Form II. In some embodiments, the liver disorder is selected from liver inflammation, liver fibrosis, alcohol induced fibrosis, steatosis, alcoholic steatosis, primary sclerosing cholangitis (PSC), primary biliary cirrhosis (PBC), non-alcoholic fatty liver disease (NAFLD), and non-alcoholic steatohepatitis (NASH). In some embodiments, the liver disorder is NAFLD or NASH. In some embodiments, the liver disorder is NAFLD. In some embodiments, the liver disorder is NASH. In some embodiments, the patient has had a liver biopsy. In some embodiments, the method further comprises obtaining the results of a liver biopsy.

In some embodiments, provided is a method of impeding or slowing the progression of NAFLD to NASH in a patient (e.g., a human patient) in need thereof comprising administering a therapeutically effective amount of Form II.

Methods of Manufacturing a Medicament

In some embodiments, provided is use of Form II in the manufacture of a medicament for use in a method disclosed herein.

Kits

Also provided are articles of manufacture and kits comprising any of the polymorphic forms or compositions provided herein. The article of manufacture may comprise a container with a label. Suitable containers include, but are not limited to, bottles, vials, and test tubes. The containers may be formed from a variety of materials such as glass or plastic. The container may hold a pharmaceutical composition provided herein. The label on the container may indicate that the pharmaceutical composition is used for treating a condition described herein, and may also indicate directions for either in vivo or in vitro use.

In one aspect, provided herein are kits comprising a polymorphic form or composition described herein and instructions for use. A kit may additionally contain any materials or equipment that may be used in the administration of the polymorphic forms or composition, such as vials, syringes, or IV bags. A kit may also contain sterile packaging.

EXAMPLES

The following examples are provided to further aid in understanding the embodiments disclosed in the application, and presuppose an understanding of conventional methods well known to those persons having ordinary skill in the art to which the examples pertain. The particular materials and conditions described hereunder are intended to exemplify particular aspects of embodiments disclosed herein and should not be construed to limit the reasonable scope thereof.

The following abbreviations may be used herein:

| | |
|---|---|
| XRPD | X-Ray Powder Diffraction |
| DSC | Differential Scanning Calorimetry |
| TGA | Thermogravimetric Analysis |
| RT | Room Temperature |
| ACN | Acetonitrile |
| EA | Ethyl Acetate |
| 2-MeTHF | 2-Methyltetrahydrofuran |
| MeOH | Methanol |
| THF | Tetrahydrofuran |
| TsOH | p-Toluenesulfonic Acid |
| TsOH•H2O | p-Toluenesulfonic Acid Monohydrate |
| MIBK | Methyl Isobutyl Ketone |
| MTBE | Methyl Tert-butyl Ether |

The polymorphic forms of Compound I tosylate were characterized by various analytical techniques, including XRPD, DSC, and TGA, using the procedures described below.

XRPD

XRPD analyses were performed with techniques and equipments known in the art with Cu K-alpha radiation.

DSC

DSC analyses were performed with techniques and equipments known in the art. Each sample was heated from 30° C. to 300° C. at a rate of 10° C./min.

TGA

TGA experiments were performed with techniques and equipments known in the art. Each sample was heated from RT to 300° C. at a rate of 10° C./min.

Example 1. Preparation of Form II

Solution of Compound I tosylate in different solvents were prepared at room temperature and filtered through 0.45 μm nylon syringe filter into clean vessels. Solvents were evaporated in the fume hood for 3 days. All solids were characterized by XRPD. The results are provided in Table 2.

TABLE 2

| Solvent | Result |
|---|---|
| MeOH | Form I |
| Acetone | Form I |

TABLE 2-continued

| Solvent | Result |
| --- | --- |
| ACN:water (95:5, v/v) | Form II |
| THF:water (95:5, v/v) | Form I |

Solution of Compound I tosylate in different solvents were prepared at room temperature (50° C. for acetone) and filtered through 0.45 μm nylon syringe filter into clean vessels. Different anti-solvents were added to precipitate out solids. The mixtures were placed in the fume hood for 3 days. The samples were centrifuged and the supernatants were removed. All solids were characterized by XRPD. The results are provided in Table 3.

TABLE 3

| Solvent | Target Con. (mg/mL) | Anti-solvent | Result |
| --- | --- | --- | --- |
| MeOH | 200 | MIBK | Form I |
|  |  | EA | Form I |
|  |  | 2-MeTHF | Form I |
|  |  | MTBE | Form I |
|  |  | Heptane | — |
| Acetone | 25 | Toluene | Form I |
|  |  | EA | Form I |
|  |  | 2-MeTHF | Form I |
|  |  | MTBE | Form I |
|  |  | Heptane | Form I * |
| ACN:water (95:5, v/v) | 100 | MIBK | Form I |
|  |  | EA | Form I |
|  |  | 2-MeTHF | Form II |
|  |  | MTBE | Form I |
|  |  | Heptane | — |
| THF:water (95:5) | 100 | MIBK | Form I |
|  |  | EA | Form I |
|  |  | Toluene | Form I |
|  |  | MTBE | Form I |
|  |  | Heptane | — |

\* minor difference due to the crystal habit.
—: Clear solution or oil

Form II was analyzed by XRPD, DSC, and TGA. FIG. 1 shows an XRPD pattern of Form II. FIG. 2 shows a DSC graph of Form II. As shown in the DSC graph, an endotherm onset at about 123° C. and an endotherm onset at about 174° C. were observed. FIG. 2 also shows a TGA graph of Form II.

Example 2. Large-Scale Preparation of Form II

Compound I in EA solution (20.70 kg, 10.7% w/w) was charged in a 1000 L glass lined reactor. TsOH in EA solution (prepared by charging 13.60 kg of TsOH·H₂O and 75 kg of EA in a 500 L glass lined reactor and stirred at 35-40° C. for 30-60 minutes) was charged slowly at 20-25° C. in 2-4 hours. The mixture was stirred at 20-25° C. for 5-8 hours and then filtered via a 250 L Hastelloy alloy dryer. The wet cake was rinsed with EA and dried. The resulting solid was characterized by XRPD and confirmed to be Form II.

Example 3. Competitive Slurry Study

Competitive slurry experiments were performed at 25° C. and 50° C. Saturated solutions of Form I in ACN and acetone at 25° C. and 50° C. were prepared. About 15 mg of Form I and Form II were weighted into the solutions respectively, and the suspensions were slurried for 1 or 3 days at 800 rpm. As determined by XRPD, a mixture of Form I and Form II could be completely converted to Form II at both temperatures, indicating that Form II was more thermodynamically stable at a temperature of 50° C. or below. The results are summarized in Table 4.

TABLE 4

| Starting Material | Solvent | Temperature (° C.) | Slurry time (days) | XRPD Pattern (wet cake) |
| --- | --- | --- | --- | --- |
| Form I + Form II | ACN | 25 | 1 | Form I + Form II |
|  |  |  | 3 | Form II |
|  |  | 50 | 1 | Form II |
|  | Acetone | 25 | 1 | Form II |
|  |  | 50 | 1 | Form I + Form II |
|  |  |  | 3 | Form II |

All documents, including patents, patent application and publications cited herein, including all documents cited therein, tables, and drawings, are hereby expressly incorporated by reference in their entirety for all purposes.

While the foregoing written description of the polymorphic forms, uses, and methods described herein enables one of ordinary skill in the art to make and use the polymorphic forms, uses, and methods described herein, those of ordinary skill in the art will understand and appreciate the existence of variations, combinations, and equivalents of the specific embodiments, methods, and examples herein.

The invention claimed is:

1. A polymorph of (2E)-3-fluoro-2-({[2-(4-methoxypiperidin-1-yl)pyrimidin-5-yl]oxy}methyl)prop-2-en-1-aminium 4-methylbenzenesulfonate:

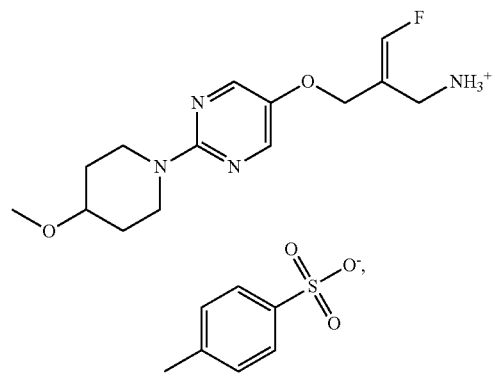

characterized as having an X-ray powder diffraction (XRPD) pattern comprising peaks at angles 2-theta of 13.7±0.2, 18.0±0.2, and 25.5±0.2 degrees.

2. The polymorph of claim 1, characterized as having an XRPD pattern comprising peaks at angles 2-theta of 8.3±0.2, 13.7±0.2, 18.0±0.2, 18.3±0.2, and 25.5±0.2 degrees.

3. The polymorph of claim 1, characterized as having an XRPD pattern substantially as shown in FIG. 1.

4. The polymorph of claim 1, characterized as having an endotherm onset at about 123° C. and/or an endotherm onset at about 174° C. as determined by differential scanning calorimetry (DSC).

5. The polymorph of claim 1, characterized as having a DSC graph substantially a shown in FIG. 2.

6. A method of preparing the polymorph of claim 1, comprising: evaporating a solution of (2E)-3-fluoro-2-({[2-(4-methoxypiperidin-1-yl)pyrimidin-5-yl]oxy}methyl) prop-2-en-1-aminium 4-methylbenzenesulfonate in a solvent, wherein the solvent comprises acetonitrile (ACN) and water.

7. The method of claim 6, wherein the volume ratio of ACN to water is about 95:5.

8. A pharmaceutical composition comprising the polymorph of claim 1, and a pharmaceutically acceptable carrier.

9. The pharmaceutical composition of claim 8, wherein the pharmaceutical composition is substantially free of other polymorphic forms of (2E)-3-fluoro-2-({[2-(4-methoxypiperidin-1-yl)pyrimidin-5-yl]oxy}methyl)prop-2-en-1-amine or a salt thereof.

10. A method of treating a liver disorder in a subject in need thereof, comprising administering a therapeutically effective amount of the polymorph of claim 1.

11. The method of claim 10, wherein the liver disorder is liver inflammation, liver fibrosis, alcohol induced fibrosis, steatosis, alcoholic steatosis, primary sclerosing cholangitis (PSC), primary biliary cirrhosis (PBC), non-alcoholic fatty liver disease (NAFLD), or nonalcoholic steatohepatitis (NASH).

12. The method of claim 11, wherein the liver disorder is NASH.

13. A method of preparing the polymorph of claim 1, comprising: stirring a mixture comprising (2E)-3-fluoro-2-({[2-(4-methoxypiperidin-1-yl)pyrimidin-5-yl]oxy}methyl)prop-2-en-1-aminium 4-methylbenzenesulfonate and a solvent, wherein the solvent comprises ACN and water or the solvent comprises ethyl acetate.

14. The method of claim 13, wherein the volume ratio of ACN to water is about 95:5.

15. A method of preparing the polymorph of claim 1, comprising: adding an anti-solvent to a solution of (2E)-3-fluoro-2-({[2-(4-methoxypiperidin-1-yl)pyrimidin-5-yl]oxy}methyl)prop-2-en-1-aminium 4-methylbenzenesulfonate in a solvent, wherein the solvent comprises ACN and water and wherein the anti-solvent comprises 2-methyltetrahydrofuran (2-MeTHF).

16. The method of claim 15, wherein the volume ratio of ACN to water is about 95:5.

17. The polymorph of claim 1, characterized as having an XRPD pattern comprising peaks at angles 2-theta of 8.3±0.2, 13.7±0.2, 18.0±0.2, 18.3±0.2, 19.6±0.2, 20.6±0.2, and 25.5±0.2 degrees.

18. The polymorph of claim 1, characterized as having an XRPD pattern comprising peaks at angles 2-theta of 8.3±0.2, 13.7±0.2, 18.0±0.2, 18.3±0.2, 19.6±0.2, 19.9±0.2, 20.6±0.2, 21.4±0.2, 25.5±0.2, and 27.0±0.2 degrees.

* * * * *